United States Patent
Sokoloff et al.

(10) Patent No.: US 7,875,617 B2
(45) Date of Patent: Jan. 25, 2011

(54) 3,4-DIHYDRO-2-NAPHTHAMIDE DERIVATIVES AS SELECTIVE DOPAMINE D3 LIGANDS

(75) Inventors: Pierre Sokoloff, Le Plessis Bouchard (FR); Catherine Pilon, Antony (FR); André Mann, Ostwald (FR); Angéle Schoenfelder, Lampertheim (FR); Fabrice Garrido, Strasbourg (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 335 days.

(21) Appl. No.: 11/814,428

(22) PCT Filed: Jan. 20, 2006

(86) PCT No.: PCT/IB2006/000088
§ 371 (c)(1),
(2), (4) Date: Apr. 21, 2008

(87) PCT Pub. No.: WO2006/077487
PCT Pub. Date: Jul. 27, 2006

(65) Prior Publication Data
US 2009/0124630 A1    May 14, 2009

(30) Foreign Application Priority Data
Jan. 24, 2005   (EP) .................. 05290156

(51) Int. Cl.
*A61K 31/4965* (2006.01)
*C07D 295/00* (2006.01)

(52) U.S. Cl. ................... 514/255.03; 544/393
(58) Field of Classification Search ............ 514/255.03; 544/393
See application file for complete search history.

(56) References Cited

U.S. PATENT DOCUMENTS

| 5,407,823 A | 4/1995 | Sokoloff et al. |
| 5,872,119 A * | 2/1999 | Wermuth et al. ....... 514/255.03 |
| 6,828,325 B2 | 12/2004 | Feenstra et al. |

FOREIGN PATENT DOCUMENTS

| EP | 0 189 612 | * 12/1985 |
| EP | 0 189 612 | 8/1986 |
| EP | 0 900 792 | 3/1999 |
| WO | WO-92/07937 | 5/1992 |
| WO | WO-03/028728 | 4/2003 |
| WO | WO-2004/084952 | 10/2004 |

OTHER PUBLICATIONS

Le Foll, et al., Neuroadaptations to Hyperdopaminergia in Dopamine D3 Receptor-deficient Mice, Life Sciences, 76, 1281-1296 (2005).*

* cited by examiner

*Primary Examiner* — James O Wilson
*Assistant Examiner* — Erich A Leeser
(74) *Attorney, Agent, or Firm* — B. Aaron Schulman; Terry L. Wright; Stites & Harbison PLLC (57) ABSTRACT

The invention relates to 3,4-dihydro-2-naphthamide derivatives of formula (I), pharmaceutical compositions containing them and their therapeutic applications as partial agonists or antagonists of the dopamine D3 receptor for the treatment of neuropsychological disorders.

11 Claims, 3 Drawing Sheets

3,4-DIHYDRO-2-NAPHTHAMIDE DERIVATIVES AS SELECTIVE DOPAMINE D3 LIGANDS

The invention relates to 3,4-dihydro-2-naphthamide derivatives, processes for their preparation, pharmaceutical compositions containing them and their therapeutic applications as partial agonists or antagonists of the dopamine D3 receptor (DRD3) for the treatment of various neuropsychological disorders.

Schizophrenia is a term used to describe a group of illnesses of unknown origin, which affects approximately 1% of the general population. This condition is characterized by a variety of symptoms, which are classified as positive symptoms (disordered thought, hallucinations and delusions) and negative symptoms (social withdrawal and blunted affect), has an age of onset in adolescence or early adulthood and persists for many years.

Patients with schizophrenia can be successfully treated with medications called neuroleptics, also known as antipsychotics. The therapeutic effect of antipsychotics is generally believed to be exerted through blockade of receptors for the brain neurotransmitter dopamine. There are five known dopamine receptor subtypes, named D1, D2, D3, D4 and D5 (Sokoloff et al., 1995) and conventional antipsychotics are antagonists of both D2 and D3 receptors. However, antipsychotics are frequently responsible for undesirable extrapyramidal side effects (EPS) and abnormal movements called tardive dyskinesias, which are attributed to blockade of dopamine D2 receptors in the striatal region of the brain. Blockade of the dopamine D3 receptor subtype has been suggested as being responsible for the therapeutic effects of antipsychotics (Schwartz, 2003). Thus, drugs that selectively modulate D3 receptor function are considered effective antipsychotics free from the neurological side effects displayed by conventional antipsychotics (international patent applications WO 91/15513 and WO 92/07937).

Selective modulation of D3 receptors can be obtained with drugs that selectively bind to D3 receptors and act either as antagonists or partial agonists. The antipsychotic-like activity of both D3 receptor partial agonists and antagonists can be revealed by using mouse models of schizophrenia (Leriche et al. (2003) and international patent application WO2004084952).

Moreover, it has recently been shown that selective blockade of D3 receptors, but not concomitant blockade of D2 and D3 receptors, increases extracellular levels of dopamine and acetylcholine, another transmitter, in the media prefrontal cortex (Lacroix et al., 2003). Dopamine and acetylcholine in this brain region are essential for cognitive function. Therefore, it is considered that selective D3 receptor antagonists can improve cognition, which is impaired in schizophrenia, as well as in neurodegenerative disorders such as Alzheimer disease.

Depression is a frequent mood disorder characterized by feelings of intense sadness or pessimistic worry, self-depreciation, often accompanied by loss of drive, enthusiasm and libido. The inability to gain pleasure from normally pleasurable experiences, also known as anhedonia, is also considered as a core symptom of depression. Considerable emphasis has been placed upon the putative role of dopamine neurons projecting to a brain region called the nucleus accumbens, in appetitive motivation (Koob, 1992; Salamone, 1994). Hence, these neurons have been suggested to be involved in the neurobiology of depression, particularly anhedonia, and the therapeutic actions of some antidepressant drugs (Kapur and Mann, 1992; Salamone, 1994; Willner, 1997). Moreover, it has been more recently shown that various antidepressant treatments selectively increase the level of D3 receptors in the nucleus accumbens (Lammers et al., 2000), suggesting that a mode of action of antidepressant treatment is to increase D3 receptor function that is presumably deficient in depression. Increasing D3 receptor function can also be achieved with D3 receptor partial agonists with high intrinsic activity, which, therefore, could be an effective treatment of this condition.

Drug addiction, also known as drug dependence, is a chronic, relapsing disorder in which compulsive drug-seeking and drug-taking behaviors persist despite negative consequences (Association, 2000; Deroche-Gamonet et al., 2004; Vanderschuren and Everitt, 2004). Drug-seeking, craving and relapse can be triggered by environmental stimuli that have acquired motivational salience through repeated associations with a self-administered drug in humans and animals (Childress et al., 1999; Robinson and Berridge, 1993) or animals (Goldberg and Gardner, 1981; Arroyo et al., 1999). Highly selective partial agonists or antagonists at the D3 receptor specifically reduce responses triggered by cocaine-(Pilla et al., 1999; Le Foll et al., 2002; Vorel et al., 2002), opiate-(Frances et al., 2004) or nicotine-(Le Foll et al., 2003) associated stimuli, while having no influence on primary rewarding effects of drugs. Moreover, the density of D3 is elevated in long-term cocaine abusers (Staley and Mash, 1996). It is therefore considered that D3 receptor partial agonists or antagonists are effective medications for aiding abstinence and reduce relapse in drug addiction.

Parkinson's disease is a disorder characterized by the occurrence of tremor, rigidity and akinesia (the difficulty to initiate and operate movements). The disease is caused by degeneration of dopamine neurons. Therapy of Parkinson's disease is based on dopamine substitution, which is achieved by administration of either L-dihydroxyphenylamine (L-DOPA) or direct dopamine agonists. However, long term use of L-DOPA is associated in a significant number of affected patients with the occurrence of abnormal movements called dyskinesia. It has recently been shown in a non-human primate model of Parkinson's disease that modulating D3 receptor function with a D3 receptor partial agonist alleviates dyskinesia (Bezard et al., 2003). Therefore, the compounds described in the present document are considered as adjuncts for therapy of Parkinson's disease.

A mutation in the D3 receptor gene is associated and co-segregates with essential tremor, a frequent and inherited movement disorder that is characterized by tremor of a body part in the absence of any other neurological disorder (Lucotte et al., 2004). The mutation increases the function of the D3 receptor. It is therefore considered that normalizing the D3 receptor function by using D3 receptor partial agonists or antagonists is an effective treatment of essential tremor.

The present invention relates to new chemical compounds derived from 3,4-dihydro-2-naphthamides and their therapeutic applications, in particular as selective dopaminergic agents. Recently naphthamides have been described as selective D3 ligands (U.S. Pat. No. 5,872,119). These compounds are useful as antipsychotic agents and for the treatment of disorders related to dopaminergic blockade. It is in this state of knowledge that the inventors have demonstrated in an entirely surprising and unexpected way the 3,4-dihydro-2- naphthamide of formula (I) given below behaved selectively as more selective ligands of the D3 receptor and more powerful partial agonists.

DEFINITIONS

As used herein, the term "dopamine D3 receptor", "D3 receptor", or "DRD3" denotes a subtype of dopamine receptor principally expressed in the limbic system (Sokoloff et al., 1990). The D3 receptor has been further described in the international patent application WO 91/15513.

As used herein, the term "D3 receptor partial agonist" denotes a compound that forms a complex with DRD3 and acts as a mixed agonist-antagonist. In vitro, a partial agonist of DRD3 produces in a cell expressing DRD3 an active response, of which the maximal intensity is lower than that produced by dopamine or its full agonist, for instance quinpirole (trans-(−)-4-aR-4,4a,5,6,7,8,8a,9-octahydro-5-propyl-1H(or 2H)-pyrazolo[3,4-g]quinoline). A D3 receptor partial agonist is also able to partially inhibit the response produced by dopamine or its full agonists. In vivo, a DRD3 partial agonist produces dopaminomimetic responses, especially when dopamine is depleted such as in 6-hydroxydopamine-lesioned rats or in 1-methyl-4-phenyl-1,2,3,6-tetrahydropyridine (MPTP)-treated monkeys. Additionally, in vivo a DRD3 partial agonist may act as an antagonist, especially when DRD3 is subject to a sustained stimulation by dopamine.

A "D3 receptor antagonist" denotes a molecule that forms a complex with DRD3 and that is capable of inhibiting an active response triggered by dopamine or its agonists from a cell expressing DRD3.

An "alkyl" means an aliphatic, saturated hydrocarbon group which may be straight or branched, having about 1 to about 5 carbon atoms in the chain. Preferred alkyl groups have 1 or 2 carbon atoms in the chain. Branched means that one or more lower alkyl groups such as methyl, ethyl or propyl are attached to a linear alkyl chain. "Lower alkyl" means 1 or 2 carbon atoms in the chain which may be straight or branched. "Higher alkyl" denotes chains having from 3 to 5 carbon atoms in the chain which may be straight or branched. Exemplary alkyl groups include methyl, cyclopropylmethyl, ethyl, n-propyl, i-propyl, n-butyl, t-butyl, n-pentyl, 3-pentyl.

An "halogen atom" denotes a bromine, chlorine, iodine or fluorine atom. A preferred halogen atom is selected from the group consisting of bromine, chlorine, and fluorine atoms.

A "perfluoroalkyl group" denotes an alkyl group, as herein described, in which all hydrogen atoms have been replaced with fluorine atoms. Preferred perfluoroalkyl group includes a trifluoromethyl group or a perfluoroethyl group.

"Alkoxy" means an alkyl-O— group wherein the alkyl group is as herein described. Exemplary alkoxy groups include methoxy, ethoxy, n-propoxy, i-propoxy, n-butoxy and pentoxy.

"Alkylthio" means an alkyl-S— group wherein the alkyl group is as herein described. Exemplary alkylthio groups include methylthio, ethylthio, i-propylthio, butylthio and pentylthio.

"Alkylsulfonyl" means an alkyl-SO₂— group wherein the alkyl group is as herein described. Exemplary alkylsulfonyl groups include methylsulfonyl, ethylsulfonyl, propylsulfonyl, butylsulfonyl and petylsulfonyl.

As used herein, the term "salts" means inorganic and organic acid addition salts, and base addition salts, of compounds of the present invention. Preferably the salts are pharmaceutically acceptable, i.e. they are relatively non-toxic for the patient to which they are administered. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate salts, and the like. (See, for example S. M. Berge, et al., <<Pharmaceutical Salts,>> J. Pharm. Sci., 66: p. 1-19 (1977)). Base addition salts include pharmaceutically acceptable metal and amine salts. Suitable metal salts include the sodium, potassium, calcium, barium, zinc, magnesium, and aluminum salts. Suitable amine base addition salts are prepared from amines which have sufficient basicity to form a stable salt, and preferably include those amines which are frequently used in medicinal chemistry because of their low toxicity and acceptability for medical use. These include ammonia, ethylenediamine, N-methyl-glucamine, ornithine, choline, N,N'-dibenzylethylenediamine, chloroprocaine, diethanolamine, procaine, N-benzylphenethylamine, diethylamine, piperazine, dimethylamine, trimethylamine, ethylamine, basic amino acids, e.g., lysine and arginine, and dicyclohexylamine, and the like.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any diluents, adjuvants, excipients, or vehicles, such as preserving agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/composition according to the present invention effective in producing the desired therapeutic effect.

According to the invention, the term "patient", or "patient in need thereof", is intended for a human or non-human mammal affected or likely to be affected with a neuropsychological disorder. Preferably, the patient is a human.

3,4-dihydro-2-naphthamides Derivatives

The invention relates to 3,4-dihydro-2-naphthamide derivatives, according to the following general formula (I):

Dihydronaphtamides in which $R^1$ and $R^2$ can be identical or different and each independently represent a hydrogen, a halogen atom, or a hydroxyl, alkoxy, nitrile, nitro or perfluoroalkyl group, or an alkyl group, eventually substituted, $R^1$ and $R^2$ substituents both being attached to the same ring of the aromatic ring of the dihydronaphthyl moiety, $R^3$ represents a hydrogen or an alkyl group in the C-1, C-3 or C-4 position of the non-aromatic ring of the dihydronaphthyl moiety in formula (I), $R^4$ and $R^5$ can be identical or different and each independently represent a hydrogen, a halogen atom, or a hydroxyl, alkoxy, nitrile, nitro, alkylthio, alkylsulfonyl, sulfoamido, carboxyamido, acetyl, hydroxyalkyl, or perfluoroalkyl group in formula (I), $R^4$ and $R^5$ also may form together a ring fused with the phenyl ring forming heterocyclic compounds such as benzodioxoles, oxindoles, benzoxazolones or quinolinones in formula (I), and salts thereof.

In the 3,4-dihydro-2-naphthamides derivatives of formula (I) according to the invention, four methylene units are placed in between the two cyclic frames. Furthermore, as compared to naphthamide derivatives previously described, the compounds according to the invention comprise a 3,4-dihydronapthyl ring instead of a fully unsaturated naphtyl ring.

The inventors have demonstrated that the compounds according to the invention, with a partial reduction of one of the aromatic ring, display higher biological activities, and higher selectivity towards the D3 receptor than the corresponding fully unsaturated naphtyl analogues. Indeed the compounds (I) are by far more selective for the D3 than for the D2 receptors, furthermore the choice of the substituents ($R^1$-$R^5$) on the 2,3-dihydro-2-naphthamide (I) modulates the whole range of pharmacological effects going from nearly full agonist to full antagonist: 3,4-dihydro-2-napthamides of formula (I) present efficacy values ranking from <0.1 (quasi antagonist) to 0.85 (quasi agonist). The reference compounds in these tests being quinpirole for the full agonist (efficacy: 1) and nafadotride for the full antagonist (efficacy: 0). The identification of these properties for the 2,3-dihydro-2-naphthamides of formula (I) are of great importance in terms of receptor activation or blockade in many brain disorders where a modulation of the dopamine level is desired.

According to an embodiment, $R^1$ to $R^5$ groups in the formula (I) are defined as follows:

$R^1$ and $R^2$ can be identical or different and each independently represent a hydrogen, bromine, chlorine or fluorine atom, or a hydroxyl, methoxy, nitrile, nitro or trifluoromethyl group, or an alkyl group, eventually substituted, $R^1$ and $R^2$ substituents both being attached to the same ring of the aromatic ring of the dihydronaphthyl moiety, $R^3$ represents a hydrogen or an alkyl, in particular: methyl, ethyl, or higher alkyl residue group in the C-1, C-3 or C-4 position of the non-aromatic ring of the dihydronaphthyl moiety in formula (I), $R^4$ and $R^5$ can be identical or different and each independently represent a hydrogen, bromine, chlorine or fluorine atom, or a hydroxyl, methoxy, nitrile, nitro, methylthio, methylsulfonyl sulfonamido, carboxyamido, acetyl, hydroxymethyl, or trifluoromethyl group in formula (I), $R^4$ and $R^5$ also may form together a ring fused with the phenyl ring forming heterocyclic moieties such as benzodioxoles, oxindoles, benzoxazolones or quinolinones in formula (I), and salts thereof.

In the formula (I), $R^1$ may also particularly represent a hydrogen atom, bromine, chlorine or fluorine atom, or a methoxy, or cyano group, or a methyl residue.

$R^2$ may also particularly represent a hydrogen atom or a methoxy group.

$R^3$ may also particularly represent a hydrogen atom or a methyl residue in the C-1, C-3 or C-4 position on the dihydronaphtyl moeity in formula (I).

$R^4$ may also particularly represent a hydrogen, or chlorine atom, or may form together with $R^5$ a ring fused with the phenyl ring forming heterocyclic moieties such as benzodioxoles in formula (I).

$R^5$ may also particularly represent a hydrogen, bromine, chlorine or fluorine atom, or a hydroxyl, methoxy, nitrile, trifluoromethyl, ethoxycarbamoyl, methoxycarbamoyl or methylsulfamido group, or a methyl residue, or may form together with $R^4$ a ring fused with the phenyl ring forming heterocyclic moieties such as benzodioxoles in formula (I).

Preferably, $R^2$, $R^3$ and $R^4$ each represent a hydrogen atom.

Also preferably, in formula (I), $R^4$ is a hydrogen atom, and $R^5$ is in meta position (C-3 or C-5 position of the phenyl ring). As described above, $R^5$ may represents a halogen atom (in particular bromine, chlorine or fluorine atom), or a hydroxyl, alkoxy (in particular methoxy), nitrile, nitro, alkylthio (in particular methylthiol), alkylsulfonyl (in particular methylsulfonyl), sulfonamido, carboxyamido, acetyl, hydroxyalkyl (in particular hydroxymethyl), or perfluoroalkyl (in particular trifluoromethyl) group. Indeed, on top of constituting compounds with higher activity and selectivity towards the D3 receptor, as compared to prior art naphthamides, these compounds also show reduced side effects. Preferably, $R^2$, and $R^3$ each represent a hydrogen atom.

A preferred compound according to the invention may be selected from the group consisting of:

(I-1) N-[4-(2-fluorophenyl)piperazin-1-yl)butyl]-3,4-dihydro-2-naphthamide, (I-2) N-[4-(2-methoxyphenyl)piperazin-1-yl)butyl]-3,4-dihydro-2-naphthamide (I-3) N-[4-(2-chlorophenyl)piperazin-1-yl)butyl]-3,4-dihydro-2-naphthamide, (I-4) N-[4-(2-bromophenyl)piperazin-1-yl)butyl]-3,4-dihydro-2-naphthamide, (I-5) N-[4-(2-hydroxyphenyl)piperazin-1-yl)butyl]-3,4-dihydro-2-naphthamide, (I-6) N-[4-(3-fluorophenyl)piperazin-1-yl)butyl]-3,4-dihydro-2-naphthamide, (I-7) N-[4-phenyl)piperazin-1-yl)butyl]-3,4-dihydro-2-naphthamide,

(I-8) N-[4-(3,4-dichlorophenyl)piperazin-1-yl)butyl]-3,4-dihydro-2-naphthamide, (I-9) N-[4-(2,3-methylenedioxyxyphenyl)piperazin-1-yl)butyl]-3,4-dihydro-2-naphthamide,
(I-10) N-[4-(3-hydroxyphenyl)piperazin-1-yl)butyl]-3,4-dihydro-2-naphthamide
(I-11) N-[4-(N-3-ethoxycarbamoylphenyl)piperazin-1-yl)butyl]-3,4-dihydro-2-naphthamide,
(I-12) N-[4-(N-3-methoxycarbamoylphenyl)piperazin-1-yl)butyl]-3,4-dihydro-2-naphthamide,
(I-13) N-[4-(N-3-methylsulfamidophenyl)piperazin-1-yl)butyl]-3,4-dihydro-2-naphthamide,
(I-14) N-[4-(3-methoxyphenyl)piperazin-1-yl)butyl]-3,4-dihydro-2-naphthamide
(I-15) N-[4-(3-methylphenyl)piperazin-1-yl)butyl]-3,4-dihydro-2-naphthamide
(I-16) N-[4-(2-methoxyphenyl)piperazin-1-yl)butyl]-3,4-dihydro-6-fluoro-2-naphthamide
(I-17) N-[4-(2-methoxyphenyl)piperazin-1-yl)butyl]-1-methyl-3,4-dihydro-2-naphthamide,
(I-18) N-[4-(2-methoxyphenyl)piperazin-1-yl)butyl]-3,4-dihydro-6-bromo-2-naphthamide,
(I-19) N-[4-(2-methoxyphenyl)piperazin-1-yl)butyl]-3,4-dihydro-6-methoxy-2-naphthamide,
(I-20) N-[4-(2-methoxyphenyl)piperazin-1-yl)butyl]-3,4-dihydro-6-methyl-2-naphthamide,
(I-21) N-[4-(2-methoxyphenyl)piperazin-1-yl)butyl]-3,4-dihydro-6-chloro-2-naphthamide,
(I-22) N-[4-(2-methoxyphenyl)piperazin-1-yl)butyl]-3,4-dihydro-6-cyano-2-naphthamide,
(I-23) N-[4-(2-methoxyphenyl)piperazin-1-yl)butyl]-3,4-dihydro-7-methoxy-2-naphthamide,
(I-24) N-[4-(2-methoxyphenyl)piperazin-1-yl)butyl]-3,4-dihydro-6,7-dimethoxy-2-naphthamide,
(I-25) N-[4-(2-fluorophenyl)piperazin-1-yl)butyl]-1-methyl-3,4-dihydro-2-naphthamide, and
(I-26) N-[4-(2-chlorophenyl)piperazin-1-yl)butyl]-1-methyl-3,4-dihydro-2-naphthamide.
(I-27) N-[4-(3-trifluoromethylphenyl)piperazin-1-yl)butyl]-3,4-dihydro-2-naphthamide
(I-28) N-[4-(3-cyanophenyl)piperazin-1-yl)butyl]-3,4-dihydro-2-naphthamide Methods of Manufacture of 3,4-dihydro-2-naphthamides Derivatives The compounds of formula (I) according to the present invention may be prepared by known methods. In the present invention two different methods were more specifically used.

Method (A) is related to the activation of the suitably substituted acid part, 3,4-dihydro-2-naphtoic acid (A1-A10) generally via its mixed anhydride obtained with isobutyl chloroformate. This preparation was performed in acetone or any compatible solvent, in basic medium, and the desired amine (B1-B11) was reacted as shown in Scheme 1:

Other methods for activating the carboxyl functional group may also be used. Indeed, any method known by the skilled in the art for the preparation of an amide is suitable, including the use of the corresponding acid chlorides. The aminopiperazines may be obtained by conventional methods, starting from commercially available phenylpiperazines, by alkylation by means of chlorobutyronitrile in basic medium in a solvent such as alcohol or equivalent. The phenylpiperazines may also be prepared by methods inspired from the patent and academic literature (Wolfe et al., 2000). The nitrile functional group was best reduced to the primary amine by catalytic hydrogenation in presence of Raney/Nickel. The reduction with LiAlH$_4$ is also another possibility (Hackling et al., 2003).

The second Method (B) is related to the transformation of the desired 3,4-dihydro-2-naphtoic acids in an amide with an halogenated atom at the distance of four methylene units (Leopoldo et al., 2002). These derivatives can be obtained by condensing the acid chlorides or their equivalents with 4-aminobutanol in basic medium to yield D1-D10, and the hydroxyl function was generally converted to a bromine atom using PPh$_3$/CBr$_4$ to yield E1-E10. CCl$_4$ in dichloromethane is also a suitable reaction. Then, the bromo derivatives E1-E10 are reacted with the phenylpiperazines C1-C6 (Scheme 2-2): C1 is commercially available and C2, C3 or C4, are prepared as indicated in the following scheme (Scheme 2-1):

Scheme 2-1.

Reagents and conditions.
i) piperazine, DMSO.
ii) Boc₂O, THF;
iii) Pd/C, H₂ (60 psi), EtOH;
iv) ClCO₂Me, triethylamine, CH₂Cl₂;
v) ClCO₂Me, triethylamine, CH₂Cl₂;
vi) ClSO₂Me, triethylamine, CH₂Cl₂
vii) HCl, ACOH.

The indications reported in the patent literature were followed for the preparation of the benzodioxoles, oxindoles, benzoxazolones or quinolinones piperazines C5 and C6 (patent application WO 02066472, patent application EP 0189612, and patent application EP 0900792). Some other piperazines used for preparing compounds of formula (I) are commercially available.

Scheme 2-2. Method (B).

A1-A10

-continued

D1-D10

E1-E10

-continued

C1-C4

1-10 to 1-13

Conditions and reagents
i). a. (ClCO)₂, CH₂Cl₂; b. NH₂(CH₂)₄OH, triethylamine;
ii). PPh₃, CBr₄, CH₂Cl₂.
iii). ClCO₂iBu, triethylamine, acetone The dihydro-naphtyl-carboxylic esters A1 et A3 are obtained following literature reports (Vebrel et al, 1982 and Wenkert at al, 1967).

The 3,4-dihydronaphtyl-carboxylic esters A2, A4, A5, A6, A7, A9 and A10 were prepared from the corresponding commercially available 2-tetralone. The formation of the triflate from the 2-tetralones and subsequent carbonylation following known procedures gave the carboxylates (Schoenberg and Heck, 1974).

Scheme 3.

Reagents and conditions
i. Tf₂O, 2,6-lutidine, DMAP, CH₂Cl₂;
ii; CO, MeOH, Pd(OAc)₂, dppp, DMF;
iii. LiOH, MeOH.

The dihydronaphtyl-carboxylic ester A8 is obtained following a known procedure (see *J. Org. Chem.* 1962, 26, 2522) from A4 as its methylester:

Scheme 4.

A-4 as ester

A8

Reagents:
i) CuCN, DMF, FeCl₃;
ii) LiOH, MeOH

Pharmaceutical Compositions and Therapeutic Applications

The activity of the derivatives of formula (I) according to the invention was evaluated with respect to cells expressing human recombinant dopamine receptors. The inhibition constants ($K_i$) were measured by inhibition of [$^{125}$I]iodosulpride binding as described by Sokoloff et al. (1992). The degree of stimulation of the D3 receptor was determined by measuring the incorporation of [$^3$H]-thymidine in NG 108-15 cells expressing the D3 receptor (Pilon et al., 1994; Sautel et al., 1995).

Furthermore the capacity of the compounds of the invention to behave as D3 receptor partial agonists or antagonists may be assessed in vivo, for instance using a screening method as described in the international patent application WO2004084952. Briefly this screening method relies on the acute or continuous administration of a mammal with a low dose of NMDA antagonist to induce a psychotic behavior which is mediated by D3 receptor. The capacity of a ligand administered to the mammal to alleviate the psychotic behavior is indicative of a ligand with anti-D3 receptor activity in vivo.

The inventors have demonstrated that compounds of formula (I) behave as powerful and selective partial agonists of dopamine at the D3 receptor.

The intrinsic activity of compounds of formula (I) vary between less than 10% and 85% as compared with the activity of quinpirole (trans-(−)-4-aR-4,4-a, 5,6,7,8,8a,9-octahydro-5-propyl-1H(or 2H)-pyrazolo[3,4-g]quinoline), which is a full DRD3 agonist and thus represent 100% intrinsic activity. For instance, the compound described in Example 4 (N-[4-[(3-hydroxyphenyl)piperazine-1-yl]butyl]-3,4-dihydronaphtalene-2-carboxamide; I-10) exhibits an affinity of 0.71 nM for the D3 receptor. Intrinsic activity of the compound of Example 4 is 0.85, and its 50% effective concentration is 2.2 nM. This same compound exhibits an apparent affinity with respect to the D2 receptor which is 160 times lower than with respect to the D3 receptor: Accordingly, it constitutes a very selective (partial) agonist of the D3 receptor. The analogue of I-10 with a fully unsaturated naphthalene group exhibits an apparent affinity of 0.74 nM for the D3 receptor and of 44 nM for the D2 receptor, and thus a selectivity ratio of 59. This result shows that the substitution of a naphthalene for a 3,4-dihydronaphtalene increases the selectivity for the D3 receptor relative to the D2 receptor.

Knowing the selective modulation of dopamine transmissions that the D3 receptor exerts in the limbic regions involved in emotional and cognitive processes (which express the D3 receptor), the compounds of the invention are suitable for therapeutic applications without interference with the dopaminergic transmissions of the extra-pyramidal, antehypophysial or vegetative (area postrema) systems. Moreover, partial agonists with low to moderate intrinsic activity can normalize transmissions of dopamine and acetylcholine in the prefrontal cortex and restore cognitive functions that depend on the activity of this brain region.

Therefore, they prevent the side effects of the existing compounds, related to the effect of the latter on the extrapyramidal, antehypophysial and vegetative areas. In addition, the D3 partial agonist nature is such as to normalize the dopaminergic transmissions without the risk of excessive activation. The derivatives of the invention can thus be used for the preparation of pharmaceutical compositions and medicaments for the treatment of neuropsychiatric conditions involving the D3 receptor, such as psychotic states.

In addition, since one effect of antidepressant drugs is to increase the level of D3 receptor in brain regions involved in reward, the compounds with high intrinsic activity described in the present invention can mimic antidepressant drugs. The derivatives of the invention can thus be used for the preparation of pharmaceutical compositions and medicaments for the treatment of depression.

Moreover, taking into account the role of the D3 receptor in drug-dependence states, pharmaceutical compositions or medicaments based on the derivatives described in the present invention can be usefully administered in states related to abstinence and/or facilitate detoxification of subjects dependent on cocaine, heroin, alcohol, nicotine, and the like. The derivatives according to the invention can also have effects on penile erection and can also be used for the preparation of pharmaceutical compositions and medicaments for the treatment of disorders of a sexual nature, in particular male impotence.

The derivatives according to the invention, as well as, generally, agonists of the D3 receptor, can also be used for a treatment complementary to the treatment of Parkinson's disease by L-DOPA. The invention thus relates to such complementary medicaments as well as to the use of partial agonists of the D3 receptor with high intrinsic activity, including the novel products of the present invention, for the preparation of a medicament for the complementary treatment of Parkinson's disease. This activity could be explained by the discovery, with respect to a non-human primate model of Parkinson's disease, that the treatment by L-DOPA induces the expression, in the cells of the caudate nucleus, putamen and internal pallidum, of D3 receptors which would underline the sensitization to the motor effects of L-DOPA, expressed by L-DOPA-induced dyskinesia.

Thus, the compounds of formula (I), bases or salts thereof, may be used for the treatment of neuropsychological disorders, in particular disorders that may be treated by partial agonists of the dopamine D3 receptor.

Hence, another object of the invention is a pharmaceutical composition that comprises at least a compound according to the invention in combination with a conventional pharmaceutically-acceptable carrier.

The invention also concerns a method of treatment of a neuropsychological disorder, which comprises administering a patient in need thereof with a compound of formula (I) in a therapeutically effective amount.

The invention further relates to the use of a compound of formula (I) for the manufacture of a medicament intended for the treatment of a patient with a neuropsychological disorder.

Examples of neuropsychological disorders according to the invention include psychosis (in particular schizophrenia), depression, essential tremor, addiction to various drugs or toxics, cognitive deficits caused by aging or neurodegenerative diseases such as Alzheimer disease, Parkinson's disease, dyskinesia, tardive dyskinesia or other movement disorders related to the use of drugs in the treatment of Parkinson's disease or schizophrenia, and sexual dysfunction.

The derivatives of formula (I) according to the invention can be administered in any suitable route, for instance by oral, systemic, parenteral, or nasal route. In particular the derivative may be administered by the oral route in an appropriate formulation. Formulations which are suitable to be administered orally to a patient include discrete units such as capsules, cachets or tablets each containing a predetermined amount of the compound of formula (I); they also include a powder or granules; as solution or a suspension in an aqueous liquid or a non-aqueous liquid; or as an oil-in-water liquid emulsion or a water-in-oil liquid emulsion.

Actual dosage levels of compounds of formula (I) in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds useful according to this invention administered to a host in single or divided doses may be in amounts, for example, of from about 0.001 to about 100 mg/kg body weight daily and preferably 0.01 to 10 mg/kg/day. The therapeutically useful doses vary with the various derivatives of the invention but, for the compound of Example 4, it may be specified that they lie between 0.05 and 5 mg/kg by the oral route.

Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The amount of each component administered is determined by the attending clinicians taking into consideration the etiology and severity of the disease, the patient condition and age, the potency of each component and other factors.

The invention will be further illustrated by the following figures and examples that do not limit the scope of the invention.

EXAMPLES

Example 1

N-[4-(2-methoxyphenyl)piperazin-1-yl)butyl]-3,4-dihydro-6-fluoro-2-naphthamide. (I-16)

To a solution of 6-fluoro-3,4-dihydro-2-naptoic acid (A2) (120 mg, 0.62 mmol) in acetone (20 mL) was added triethylamine (2 mL), the mixture was cooled at −15° C. and isobutylchloroformate (0.12 mL, 0.84 mmol) was added dropwise. After 1 h, a solution of B2 (300 mg, 0.80 mmol) in acetone was added dropwise and then the mixture was allowed to stand at room temperature for 4 h. The precipitate was filtered and the filtrate was concentrated in vacuo. The residue was taken in AcOEt and washed with $H_2O$ (2×20 mL). The organic layer was dried over $Na_2SO_4$ and concentrated in vacuo. The oily residue was purified by column chromatography eluting with AcOEt/MeOH 90/10 to yield the title compound (100 mg, 33%, mp 128° C.). $^1$H NMR (200 MHz, CDCl$_3$) δ 1.69-1.77 (m, 4H), 2.49-2.54 (m, 2H), 2.55-2.60 (m, 2H), 2.68 (s, 4H), 2.86-2.92 (m, 2H), 3.06-3.12 (m, 4H), 3.42-3.58 (m, 2 H), 3.88 (s, 3H), 6.85-6.99 (m, 4H), 7.19-7.22 (m, 1H), 7.29-7.33 (m, 1H), 7.80 (s, 1H), 7.83-7.88 (m, 1H), 8.41 (s, 1H). $^{13}$C NMR (50 MHz, CDCl$_3$) δ 23.1, 24.8, 27.9, 28.4, 40.1, 40.5, 50.9, 53.9, 55.7, 58.5, 111.6, 118.5, 121.4, 123.4, 125.2, 127.7, 128.2, 129.6, 129.8, 130.2, 131.7, 141.6, 152.7, 168.4.

1. Methoxy 3,4-dihydro-6-fluoro-2-naphtoate

To a stirred solution of 6-fluoro-2-tetralone (660 mg, 4 mmol) and 2,6-dimethylpyridine (500 mg) in $CH_2Cl_2$ (10 mL) were added at −30° C. 4-N,N-dimethylaminopyridine (100 mg) and trifluoromethanesulfonic anhydride (0.7 mL). Then the reaction was left at room temperature for 10 h. The mixture was quenched with $H_2O$ (5 mL) and extracted with $CH_2Cl_2$ (3×20 mL). The organics were washed with brine, $Na_2SO_4$ and concentrated in vacuo. The obtained trifluoromethane sulfonate was used in the next step without purification and directly dissolved in DMF (5 ml). To this solution was added Pd(OAc)$_2$ (30 mg, 0.13 mmol), 1,3-bis(diphenylphosphino)propane (dppp, 54 mg, 0.13 mmol), triethylamine (0.4 mL), methanol (5 mL) and the mixture was heated at 70° C. under an atmosphere of CO for 10 h. The cooled solution was diluted with Et$_2$O washed three times with water, dried over Na$_2$SO$_4$, concentrated in vacuo. The residue was purified by chromatography with silica gel eluting with hex/AcOEt: 4/1, to give the title compound as a colourless oil. $^1$H NMR (200 MHz, CDCl$_3$) δ 2.58-2.63 (m, 2H), 2.84-2.90 (m, 2H), 3.82 (s, 3H), 6.87-6.90 (m, 2H), 7.15-7.20 (m, 1H), 7.50 (s, 1H).

2. 3,4-Dihydro-6-fluoro-2-naptoic Acid. (A2)

LiOH (100 mg) was added to a stirred solution of 3,4-dihydro-6-fluoro-2-napthoic methyl ester (164 mg, 0.80 mmol) in a mixture of MeOH—H$_2$O (4/1, 30 mL). The mixture was stirred at room temperature overnight. After concentration the residue was diluted in H$_2$O, washed with Et$_2$O and the aqueous layer was acidified with aqueous HCl (10% in H$_2$O) until pH 1. The acid was extracted with AcOEt (3×5 mL), the organics were washed twice with H$_2$O, dried over Na$_2$SO$_4$ and the solvent evaporated to leave white crystals of A2 (150 mg, 96%), used without further purification in the next step.

3. 1-N(3-cyanopropyl)-4-N(2-methoxyphenyl)piperazine

A mixture of 2-methoxy-phenylpiperazine (8 g), K$_2$CO$_3$ (2.5 eq) and 4-bromobutyronitrile (1.05 eq) in CH$_3$CN (150 mL) was refluxed for 10 h. After filtration and concentration in vacuo, the residue is taken up in AcOEt (1000 ml), washed with H$_2$O, the organic layer is washed with aqueous HCl (50 mL, 1 M). Then the acid layer is washed with AcOEt (2×20 ml) and neutralized with aqueous NH$_3$ (28% in H$_2$O) until pH 11. Extraction is carried out with AcOEt, the organic layer is dried with Na$_2$SO$_4$ and concentrated in vacuo. The residual solid is crystallized in hexane to give the title compound (6.8 g, 75%, mp 74° C.). $^1$H NMR (200 MHz, CDCl$_3$) δ 1.80-1.94 (m, 2H), 2.43-2.57 (m, 4H), 2.62-2.67 (m, 4H), 3.09 (m, 4H), 3.87 (s, 3H), 6.85-7.04. $^{13}$C NMR (50 MHz, CDCl$_3$) δ 14.9, 22.7, 50.5, 53.2, 55.3, 56.3, 111.1, 118.1, 119.8, 120.9, 122.9, 141.1, 152.2.

4. 1-N(4-aminobutyl)-4-N(2-methoxyphenyl)piperazine. (B2)

1-N(3-cyanopropyl)-4-N(2-methoxyphenyl)piperazine (5 g) was dissolved in a mixture of MeOH and aqueous ammonia (28%) in 1/1 ratio (20 mL) and the mixture is shook in a Parr apparatus in presence of Raney/Ni (500 mg) at 60 psi for 18 h. The catalyst is removed by filtration and the filtrate concentrated in vacuo. The residue is taken in AcOEt, the organic layer is washed three times with H$_2$O, dried over Na$_2$SO$_4$ and concentrated. The oily residue is dissolved in EtOH and aqueous HCl (37%, 15 mL) is added. The obtained hydrochloride salt is crystallized in Et$_2$O to give the title compound B2 (4.5 g, 81%) as crystals. $^1$H NMR (200 MHz, CDCl$_3$) δ 1.48-1.64 (m, 4H), 2.16 (s, 2H), 2.36-2.43 (m, 2H), 2.57-2.62 (m, 4H), 2.69-2.76 (m, 2H), 3.18-3.23 (m, 4H), 3.79 (s, 3H), 6.40-6.56 (m, 3H), 7.20 (t, 1H). $^{13}$C NMR (50 MHz, CDCl$_3$) δ 24.2, 31.6, 42.0, 49.0, 53.1, 55.1, 58.4, 102.4, 104.3, 108.8, 129.7, 152.6, 160.5.

Example 2

N-[4-[4-(2-methoxy-phenyl)piperazin-1-yl]butyl]-1-methyl-3,4-dihydronaphthalene-2-carboxamide. (I-17)

Triethylamine (2 mL) was added to a solution of 1-methyl 3,4-dihydro 2-naphtoic acid (A3) (150 mg, 0.80 mmol) in dry acetone (10 mL). The mixture was cooled to −15° C. and isobutylchloroformate (0.12 ml, 0.84 mmol) was added dropwise. After 1 h, B3 (300 mg, 0.80 mmole) was then added and the mixture was allowed to stand at room temperature for 4 h. The precipitate was filtered and the filtrate was concentrated in vacuo. The residue was taken up in AcOEt, and washed twice with water. The organic layer was dried over $Na_2SO_4$ and concentrated in vacuo. The residue was adsorbed on silica gel and subjected to purification by chromatography: AcOEt-MeOH:90/10). 200 mg of white crystals were obtained. (mp 128, 60%). $^1$H NMR (300 MHz, $CDCl_3$): δ 1.66-1.70 (m, 4H), 2.19 (s, 3H), 2.47-2.52 (m, 4H), 2.60-2.65 (m, 4H), 2.77-2.85 (t, 2H), 3.00-3.05 (t, 4H), 3.39-3.44 (m, 2H), 6.60-6.68 (m, 1H), 6.73 (t, 1H), 6.91-7.06 (m, 3H), 7.12-7.33 (m, 4H).

1. Aceto-α-phenyl-γ-butyric Acid Ethyl Ester

Ethyl acetoacetate (17.15 g, 0.13 mmol) was added dropwise to a stirred solution of sodium ethylate (prepared by dissolution of 2.8 g of sodium in 60 mL of dry ethanol). The mixture was warmed at 60° C. for 30 min. After cooling, phenethylbromide (23.5 g, 0.115 mol) was added dropwise over 1 h and the mixture was then refluxed for 15 h. After cooling, the solvent was removed in vacuo and the residue was taken of with $H_2O$, acidified to pH 3 with diluted hydrochloric acid and then extracted diethylether (2×20 mL). The organic layer was washed $H_2O$, dried over Na2SO4 and concentrated in vacuo. The residue was purified by distillation under reduced pressure (106° C./0.1 mm Hg) to give a colourless oil (71%). $^1$H NMR (300 MHz, $CDCl_3$) δ 1.27-1.32 (t, 3H), 2.18-2.24 (m, 2H), 2.22 (s, 3H), 2.61-2.70 (m, 2H), 3.42-3.47 (m, 1H), 4.18-4.25 (m, 2H), 7.18-7.32 (m, 5H).

2. 1-Methyl 3,4-dihydro Naphthalene 2-carboxylic Acid (A3)

Aceto-α-phenyl-γ-butyric acid ethyl ester (5 g, 27 mmol) was added dropwise to $H_2SO_4$ (30 mL) at −20° C. The mixture is stirred at this temperature for 4 h and was then cautiously hydrolyzed in of a cold water (300 mL). The white precipitate was filtered of and dried overnight. The crude acid was recrystallized with a benzene-hexane mixture to yield white crystals (81%. mp. 127° C.). $^1$H NMR (200 MHz, $CDCl_3$): δ 2.57 (s, 3H), 2.63-2.68 (m, 2H), 2.77-2.81 (m, 2H), 7.17-7.53 (m, 4H).

3. 1-(3-Cyanopropyl)-4-(2-fluoro-phenyl)piperazine

2-Fluorophenyl piperazine (6.5 g) are suspended in acetonitrile (50 ml), anhydrous $K_2CO_3$ (1.5 eq) and 4-bromobutyronitrile (1.05 eq) in acetonitrile (25 mL) are added dropwise. The mixture is heated at reflux for 10 h and then filtered, the filtrate is concentrated in vacuo. The residue is taken up in AcOEt and washed three times with water. The organic layer is extracted with hydrochloric acid (1M) and the aqueous acid layer is washed with AcOEt and neutralized with aqueous ammonia (28% in $H_2O$) to pH 11. The extraction is carried out with AcOEt and the organic layer is washed twice with water and dried over $Na_2SO_4$. The mixture is concentrated to give the title compound (8.35 g, 98%). $^1$H NMR (200 MHz, $CDCl_3$) δ 1.80-1.90 (m, 2 H), 2.42-2.49 (m, 2H), 2.52-2.56 (m, 2H), 2.59-2.64 (m, 4H), 3.07-3.13 (m, 4H), 6.91-7.07 (m, 4H). RMN $^{13}$C (50 MHz, $CDCl_3$): δ 14.8, 22.6, 50.4, 53.0, 56.2 115.8, 116.2 118.8, 119.7, 122.3, 122.5, 124.3, 124.4, 153.1, 158.0.

4. 1-(4-Aminobutyl) 4-(2-fluoro-phenyl)piperazine (B3)

1-(3-Cyanopropyl)-4-(2-fluoro phenyl)piperazine (2 g) was dissolved in a mixture of methanol and aqueous ammonia 28% (1-1, 20 ml) and the mixture is introduced in a Parr bottle. Then, Raney nickel (500 mg) is added as catalyst, and the mixture is hydrogenated in a Parr apparatus for 12 h under 60 psi. The catalyst is filtered of. The filtrate is evaporated in vacuo and the residue is taken of with AcOEt, the organic layer is washed three times with $H_2O$, dried over anhydrous $Na_2SO_4$ and evaporated. The residue is taken with EtOH and concentrated HCl (15 mL 37%) is added. The mixture is evaporated and the hydrochloride is crystallized in a mixture of EtOH-$Et_2O$ (1-1) to yield the title compound B3 (99%). $^1$H NMR (200 MHz, $CDCl_3$) δ: 1.44-1.61 (m, 4H), 1.88 (s, 2H), 2.37-2.45 (t, 2H), 2.60-2.65 (t, 4H), 2.65-2.72 (t, 2 H), 3.09-3.14 (t, 4H), 6.90-7.08 (m, 4H). RMN $^{13}$C (50 MHz, $CDCl_3$): δ 24.2, 31.6, 42.0, 50.4, 53.2, 58.4, 115.7, 118.8, 122.3, 124.4, 142.8, 158.1.

Example 3

N-[4-(N-3-methylsulfamidophenyl)piperazin-1-yl) butyl]-3,4-dihydro-2-naphthamide. (I-13)

A mixture of the bromide E1 (100 mg, 0.326 mmol), the N-methylsulfonamido-piperazine (C4) (107 mg, 0.326 mmol) and triethylamine (0.137 mL, 0.978 mmol) is refluxed for 16 h. The solvent is removed in vacuo. The residue is taken in $CH_2Cl_2$, washed with $H_2O$ and brine. The organic layer is concentrated and the residue is purified by chromatography eluting with AcOEt-MeOH (9/1) to yield the title compound as a solid (mp 151° C., 50 mg, 35%) $^1$H NMR ($CDCl_3$ 200 MHz): δ 1.64-1.66 (m, 4H), 2.45-2.66 (m, 6H), 2.86-2.91 (m, 2H), 3.08 (s, 3H), 3.22-3.44 (m, 10H), 6.22 (br s, 1H), 6.66-6.72 (m, 3H), 7.16-7.28 (5H). $C_{26}H_{34}N_4O_3S$ MW 482.64. MS 483 ($M^+$+1).

1. 1-N(3-nitrophenyl)-4-N-tert-butoxycarbonylpiperazine

A mixture of piperazine (12 g, 138 mmol), 1-fluoro-3-nitrobenzene (4 ml, 34 mmol) and potassium carbonate (9.60 g, 69 mmol) in DMSO (40 mL) is heated at 100° C. for 24 h. The reaction is quenched with $H_2O$ (60 mL) and extracted with $Et_2O$ (3×20 mL). The organic layer is washed with brine (20 mL) and dried over $Na_2SO_4$ and concentrated in vacuo. The residue is chromatographied on silica gel eluting with $CH_2Cl_2$/MeOH (94/6) to yield the title compound (5.15 g, 72%) as an orange solid. This solid was dissolved in $CH_2Cl_2$ and $Boc_2O$ (6 g, 130 mmol) was added. The mixture was stirred overnight. The solvent was evaporated and the residual solid was crystallized in heptane (6.80 g, 93%, mp 86° C.). $^1$H NMR (200 MHz, $CDCl_3$) δ 1.49 (s, 9H), 3.22-3.27 (m, 4H), 3.58-3.63 (m, 4H), 7.16-7.71 (m, 4H).

2. 1-(3-N-Amino-phenyl)-4-N-tert-butoxycarbonyl-piperazine

In a Parr bottle was added the nitro adduct (4 g, 13 mmol), Pd (10% on C, 400 mg) and EtOH (100 mL). The mixture was shacked overnight under a hydrogen atmosphere (50 Psi). The catalyst was eliminated by filtration, and after concentration in vacuo, the title compound gave a white solid in heptane. (3 g, 83%). $^1$H NMR (200 MHz, $CDCl_3$) δ 1.48 (s, 9H), 3.07-3.10 (m, 4H), 3.44-3.56 (m, 4H), 6.21-6.35 (m, 3 h), 7.01-7.27 (m, 1H).

3. 1-N[3-Methylsulfonaminophenyl)-4-N-terbutoxy-carbonyl-piperazine

To a solution of the above amine (400 mg, 1.44 mmol) and triethylamine (0.6 mL, 4.32 mmol) in CH$_2$Cl$_2$ (20 mL) was added at 0° C. mesyle chloride (0.13 mL, 1.30 mmol) and the mixture was stirred for 2 h. After concentration in vacuo, the residue was purified by column chromatography eluting with heptane-AcOEt (3/2) to yield the title compound (200 mg, 78%) as an oil.
$^1$H NMR (200 MHz, CDCl$_3$) δ 1.51 (s, 9H), 3.02 (s, 3H), 3.17-3.20 (m, 4 H), 3.44 (s, 1H), 3.43-3.62 (m, 4H), 6.70-6.85 (m, 3H), 7.21-7.29 (m, 1H).

4. 2-Ethoxycarbonyl-1-tetralone

To a stirred suspension of NaH (11 g, 274 mmol, 60% in oil) in toluene was added dropwise 1-tetralone (20 g, 137 mmol) in toluene (50 mL). After the complete addition, the mixture was heated at reflux for 1 h. Then at 60° C. diethyl-carbonate was added (24 g, 137 mmol) dropwise and the mixture was again heated at reflux for 2 h. The reaction was quenched with aqueous HCl (4N, 100 mL) and dilute with H$_2$O. Ether (200 mL) was added for the extraction, the organics were dried and concentrated to oil. Distillation (100° C. at 0.1 mm Hg) gave the title compound (19.1 g, 64%). $^1$H NMR (CDCl$_3$, 200 MHz): δ 1.34 (t, 3H, J 7.0 Hz), 1.38 (t, 3H, J 7.0 Hz), 2.20-3.10 (m, 4H), 3.59 (1H, dd, J 7.0 Hz J 10.0 Hz), 4.24 (1H, q, J 7.0 Hz), 4.28 (q, 1H, J 7.0 Hz), 7.29 (m, 3H), 7.78 (m, 1H), 8.01 (m, 1H), 12.5 (s, 1H). $^{13}$C NMR (CDCl$_3$, 50 MHz): δ 14.1, 14.2, 20.5, 26.36, 27.5, 27.7, 54.5. 60.4; 61.1; 96.9. 124.2, 126.5, 126.7, 127.2, 127.6; 128.7, 130.0, 130.4. 131.8. 133.7, 139.3, 143.6. 165.0, 170.1, 172.6, 193.0.

5. Ethyl 2-dihydro Naphtoate

To a stirred suspension of NaBH$_4$ (900 mg, 21.4 mmol) in EtOH (40 mL) was added a solution of the keto-ester (6.2 g, 28 mmol) in EtOH (100 mL) at −10° C. After the completion of the addition the mixture was heated at reflux for 24 h. Then the reaction was quenched with aqueous HCl (1 M). The extraction was performed with Et$_2$O (2×20 mL), the organics were dried and concentrated in vacuo. The residue was purified by chromatography eluting with Heptane-AcOEt (9/1) to yield the title compound (2 g, 40%) as an oil. $^1$H NMR (CDCl$_3$ 200 MHz): δ 1.35 (t, J 7 Hz, 3 H), 2.61-2.70 (t, J 7 Hz, 2H), 2.88-2.96 (m, 2H), 2.27-4.38 (m, 2H), 7.21-7.30 (m, 4 H), 7.57 (s, 1H). $^{13}$C NMR (CDCl$_3$ 50 MHz): δ 14.4, 22.3, 27.6, 60.6, 126.7, 128.4, 129.4, 129.7, 132.7, 136.3, 137.1, 167.4.

6. 2-Dihydronaphtoic Acid. (A1)

A mixture of the ester (1 g, 5 mmol) and LiOH (710 mg, 30 mmol) in MeOH (20 mL) was stirred at room temperature for 24 h. Evaporation of the solvent gave a residue which was taken in H$_2$O (20 mL) and Et$_2$O (30 mL). The aqueous layer was acidified at pH 1 with HCl (1 N) and then extracted with AcOEt (50 mL). The organics were dried and concentrated to give the title compound as a white solid (705 mg, 82%).

7. N-(4-bromobutyl)-dihydro-2-naphtylcarboxamide. E1

A mixture of the acid (A1) (226 mg, 1.3 mmol), oxalyl chloride (0.14 mL, 1.56 mmol) and two drops of DMF was stirred at room temperature in CH$_2$Cl$_2$ (20 mL) for 2 h. The solvent was evaporated and the residue was used in the next step. To a mixture of aminobutanol (0.13 mL, 1.43 mmol) and triethylamine (0.54 mL, 3.9 mmol) in CH$_2$Cl$_2$ (5 mL) was added a solution of the acid chloride (1.3 mmol) in CH$_2$Cl$_2$ (2 mL). After 12 h the solvent was evaporated and the residue taken in AcOEt (10 mL) washed with H$_2$O, dried and concentrated. The residual solid D1 (300 mg, 90%) was used in the next step. A solution of the hydroxy adduct (300 mg, 1.22 mmol) in CH$_3$CN (10 mL) was cooled at 0° C., and CBr$_4$ (606 mg, 1.83 mmol) and PPh$_3$ (480 mg, 1.83 mmol) were added. After 12 h stirring AcOEt (50 mL) was added and the organic layer was washed with NaOH (20 ml, 1 N), dried and concentrated in vacuo to give the title compound E1 as a solid (240 mg, 64%) after purification by chromatography. $^1$H NMR (CDCl$_3$ 200 MHz): δ 1.70-2.02 (m, 4H), 2.55-260 (m, 2H), 2.86-2.92 (m, 2H), 3.42-3.49 (m, 4H), 5.99 (s, 1H), 7.15-7.27 (m, 4H).

Example 4

N-[4-[(3-hydroxyphenyl)piperazine-1-yl]butyl]-3,4-dihydronaphtalene-2-carboxamide. (I-10)

A mixture of the bromo adduct E1 (100 mg, 0.32 mmol), of commercial 3-hydroxyphenyl piperazine (57 mg, 0.32 mmol) and triethylamine (0.07 mL, 0.5 mmol) in CH$_3$CN are reluxed during 16 h. The solvent is evaporated and the residue is taken up in CH$_2$Cl$_2$ (15 mL), washed with brine, dried and concentrated. The residue is purified by chromatography eluting with AcOEt:MeOH (9/1) to yield the titled adduct (mp 152° C., 70 mg, 54%)
$^1$H NMR (CDCl$_3$ 200 MHz): δ 1.18-1.25 (m, 2H), 1.63 (m, 3H), 2.43-2.60 (m, 8H), 2.83-2.91 (m, 2H), 3.40-3.54 (m, 6H), 6.32-6.42 (m, 4H), 7.03-7.26 (m, 5H)
MW C$_{25}$H$_{31}$N$_3$O$_2$ 405. MS 406 (M$^+$+1)

Example 5

Dihydrochloride of Ethyl 3-[−1-N-[4-N[3,4-dihydronaphtalenyl-2-carbonyl]aminobutyl]piperazin-yl]phenylcarbamate. (I-12)

A mixture of the bromo adduct E1 (100 mg, 0.32 mmol), the piperazine carbamate C3 (90 mg, 0.32 mmol) and triethylamine (0.09 mL, 0.64 mmol) in CH$_3$CN (10 ml) was refluxed for 16 h. After concentration of the solution the residue was taken up in CH$_2$Cl$_2$, washed with H$_2$O, and brinedried with Na$_2$SO$_4$. After concentration in vacuo, the residue was purified by chromatography on silica gel eluting with ACOEt/MeOH 9/1 to give the titled compound (113 mg, 74%) as an oil which converted to its di-hydrochloride salt by aqueous HCl (mp 154° C.). $^1$H NMR (CDCl$_3$ 200 MHz): δ 1.29 (t, J 8 Hz, 3H), 1.62 (m, 4H), 2.42-3.49 (m, 16H), 4.20 (q, J 8 Hz, 2H), 6.45-6.90 (m, 4-H), 7.11-7.18 (m, 4H). MW C$_2$H$_{34}$N$_4$O$_3$ 476; SM (M$^+$+1) 477

1-[3-N Carboxyethyl-phenyl)-4-terbutoxycarbonyl-piperazine

To a solution of the amine (200 mg, 0.72 mmol), triethylamine (0.27 mL, 1.96 mmol) in CH$_2$Cl$_2$ (5 mL) was added at 0° C. ethylchloroformate (0.06 mL, 0.65 mmol). The mixture was stirred for 2 h at room temperature. The solvent was evacuated and the residue taken up in Et$_2$O, washed with H$_2$O, dried and concentrated in vacuo to an oil, which was purified by column chromatography eluting with AcOEt-heptane 25/75 to give the title compound as an oil. $^1$H NMR (CDCl₃ 200 MHz): δ 1.30 (t, J 7 Hz, 3H), 1.48 (s, 9H), 3.11-3.16 (m, 4H), 3.53-3.59 (m, 4H), 6.58-6.74 (m, 3H), 7.13-7.26 (m, 1H).

1-[3-N Carboxyethyl-phenyl)-4-piperazine C3

A solution of the Boc (200 mg, 0.57 mmol) adduct was dissolved in a mixture of AcOH (15 mL) and Aqueous HCl (11 N, 7.5 mL) and the reaction was stirred for 2 h. The solvent was evaporated in vacuo to give the title compound C3 as a solid (171 mg, 93%), used in the next step.

Example 6

N-[4-[4-(3-hydroxyphenyl)piperazine-1-yl]butyl]-3,4-dihydronaphtalenyl-2-carboxamide. (I-11)

A mixture of the bromo adduct E1 (100 mg, 0.32 mmol), 3-hydroxyphenyl piperazine C1 (57 mg, 0.32 mmol) and triethylamine (0.07 ml, 0.5 mmol) in CH₃CN was refluxed for 16 h. The solvent was evacuated and the residue was purified by column chromatography eluting with AcOEt/MeOH 9/1 to give the title compound as a solid (70 mg, 54%, mp 152° C.)
¹H NMR (CDCl₃ 200 MHz): δ 1.62 (m, 4H), 2.43-4.54 (m, 16H), 6.32-646 (m, 4H), 7.03-7.26 (m, 4H). MW $C_{25}H_{31}N_3O_5$ 405. SM (M⁺+1) 496

Physical Data of the Compounds:
- (I-1) N-[4-(2-fluorophenyl)piperazin-1-yl)butyl]-3,4-dihydro-2-naphthamide
  $C_{25}H_{30}FN_3O$. MW 407, MS 408 (M⁺+1); mp 100° C.
- (I-2) N-[4-(2-methoxyphenyl)piperazin-1-yl)butyl]-3,4-dihydro-2-naphthamide
  $C_{26}H_{33}N_3O_2$. MW 419, MS 420 (M⁺+1); mp 103° C.
- (I-3) N-[4-(3-chlorophenyl)piperazin-1-yl)butyl]-3,4-dihydro-2-naphthamide
  $C_{25}H_{30}ClN_3O$. MW 423, MS 424 (M⁺+1); mp 115° C.
- (I-4) N-[4-(2-bromophenyl)piperazin-1-yl)butyl]-3,4-dihydro-2-naphthamide
  $C_{25}H_{30}BrN_3O$. MW 468, MS 469 (M⁺+1); mp 93° C.
- (I-5) N-[4-(2-hydroxyphenyl)piperazin-1-yl)butyl]-3,4-dihydro-2-naphthamide
  $C_{25}H_{31}N_3O_2$. MW: 405; mp 63° C.
- (I-6) N-[4-(3-fluorophenyl)piperazin-1-yl)butyl]-3,4-dihydro-2-naphthamide
  $C_{25}H_{30}FN_3O$. MW 412; mp 114° C.
- (I-7) N-[4-Phenylpiperazin-1-yl)butyl]-3,4-dihydro-2-naphthamide, 2HCl
  $C_{25}H_{31}N_3O.2HCl$. MW: 4611. MS 390 (M⁺+1); mp 178° C.
- (I-8) N-[4-(3,4-dichlorophenyl)piperazin-1-yl)butyl]-3,4-dihydro-2-naphthamide
  $C_{25}H_{29}Cl_2N_3O$. MW: 458, MS 459 (M⁺+1); mp 131° C.
- (I-9) N-[4-(2,3-methylenedioxyxyphenyl)piperazin-1-yl)butyl]-3,4-dihydro-2-naphthamide
  $C_{26}H_{31}N_3O_3$. MW: 433, MS 434 (M⁺+1)
- (I-10) N-[4-(3-hydroxyphenyl)piperazin-1-yl)butyl]-3,4-dihydro-2-naphthamide
  $C_{25}H_{31}N_3O_2$ mw 405 mp 152° C.
- (I-11) N-[4-(N-3-ethoxycarbamoylphenyl)piperazin-1-yl)butyl]-3,4-dihydro-2-naphthamide
  $C_{28}H_{36}N_4O_3,2HCl$. MW 549; mp 154° C.
- (I-12) N-[4-(N-3-methoxycarbamoylphenyl)piperazin-1-yl)butyl]-3,4-dihydro-2-naphthamide,
  $C_{27}H_{34}N_4O_3$. MW: 462; mp 126° C.
- (I-13) N-[4-(N-3-methylsulfamoylphenyl)piperazin-1-yl)butyl]-3,4-dihydro-2-naphthamide
  $C_{26}H_{34}N_4O_3S$. MW 482, mp 151° C.
- (I-14) N-[4-(N-3-methoxyphenyl)piperazin-1-yl)butyl]-3,4-dihydro-2-naphthamide
  $C_{26}H_{33}N_3O_2$. MW 419; mp 81° C.
- (I-15) N-[4-(3-methylphenyl)piperazin-1-yl)butyl]-3,4-dihydro-2-naphthamide
  $C_{26}H_{33}N_3O$. MW: 403; mp 104° C.
- (I-16) N-[4-(2-methoxyphenyl)piperazin-1-yl)butyl]-3,4-dihydro-6-fluoro-2-naphthamide
  $C_{26}H_{32}FN_3O_2$. MW 437; mp 128° C.
- (I-17) N-[4-(2-methoxyphenyl)piperazin-1-yl)butyl]-1-methyl-3,4-dihydro-6-fluoro-2-naphthamide
  $C_{27}H_{35}N_3O_2$. MW 433; mp 128° C.
- (I-18) N-[4-(2-methoxyphenyl)piperazin-1-yl)butyl]-3,4-dihydro-6-bromo-2-naphthamide
  $C_{26}H_{32}BrN_3O_2$. MW 498 mp 98° C.
- (I-19) N-[4-(2-methoxyphenyl)piperazin-1-yl)butyl]-3,4-dihydro-6-methoxy-2-naphthamide, 2HCl
  $C_{27}H_{25}N_3O_3,HCl$. MW 486; mp 216° C.
- (I-20) N-[4-(2-methoxyphenyl)piperazin-1-yl)butyl]-3,4-dihydro-6-methyl-2-naphthamide, 2HCl
  $C_{27}H_{35}N_3O_2$. MW 433, MS 434 (M⁺+1)
- (I-21) N-[4-(2-methoxyphenyl)piperazin-1-yl)butyl]-3,4-dihydro-6-chloro-2-naphthamide
  $C_{26}H_{32}ClN_3O_2$. MW 454; mp 98° C.
- (I-22) N-[4-(2-methoxyphenyl)piperazin-1-yl)butyl]-3,4-dihydro-6-cyano-2-naphthamide
  $C_{27}H_{32}N_4O_2$. MW 444; mp 127° C.
- (I-23) N-[4-(2-methoxyphenyl)piperazin-1-yl)butyl]-3,4-dihydro-7-methoxy-2-naphthamide
  $C_{27}H_{35}N_3O_3$. MW 449; mp 96° C.
- (I-24) N-[4-(2-methoxyphenyl)piperazin-1-yl)butyl]-3,4-dihydro-6,7-dimethoxy-2-naphthamide
  $C_{28}H_{37}N_3O_4,HCl$. MW 515; mp 241° C.
- (I-25) N-[4-(2-fluorophenyl)piperazin-1-yl)butyl]-1-methyl-3,4-dihydro-2-naphthamide
  $C_{29}H_{32}FN_3O$. MW 421; mp 94° C.
- (I-26) N-[4-(2-chlorophenyl)piperazin-1-yl)butyl]-1-methyl-3,4-dihydro-2-fluoro-2-naphthamide
  $C_{26}H_{32}ClN_3O$. MW 438; mp 76° C.
- (I-27) N-[4-(3-trifluoromethylphenyl)piperazin-1-yl)butyl]-3,4-dihydro-2-naphthamide
  $C_{26}H_{30}F_3N_3O$. MW 457; mp 106° C.
- (I-28) N-[4-(3-cyanophenyl)piperazin-1-yl)butyl]-3,4-dihydro-2-naphthamide
  $C_{26}H_{30}N_4O$ MW 414; mp 141° C.

Example 7

In vitro Activity of I-28

I-28 is one of the most D3 receptor-selective ligands known so far, with an affinity for D3 and D2 receptors of 2.1 and 318 nM, respectively.

I-28 activity in vitro towards recombinant D3 receptor has been determined using a validated mitogenesis assay which was performed as follows:

NG 108-15 cells (Hamprecht et al., 1985) were plated in 96-well plates at a density of 5,000 cells per well. After a 24 h-culture, cells were washed twice with culture medium without fetal calf serum and incubated for 16 hours with drugs in four replicates. Then [³H]thymidine (1 µCi per well) was added for 2 hours and cells were harvested by vacuum filtration through Whatman GF/C fiber filters using an automated cell harvester (Brandel-Beckman) and rinsed 10 times with 200 µl 50 mM potassium phosphate buffer containing 150 mM NaCl. Radioactivity retained on filters was counted by liquid scintagraphy.

Figure 1:
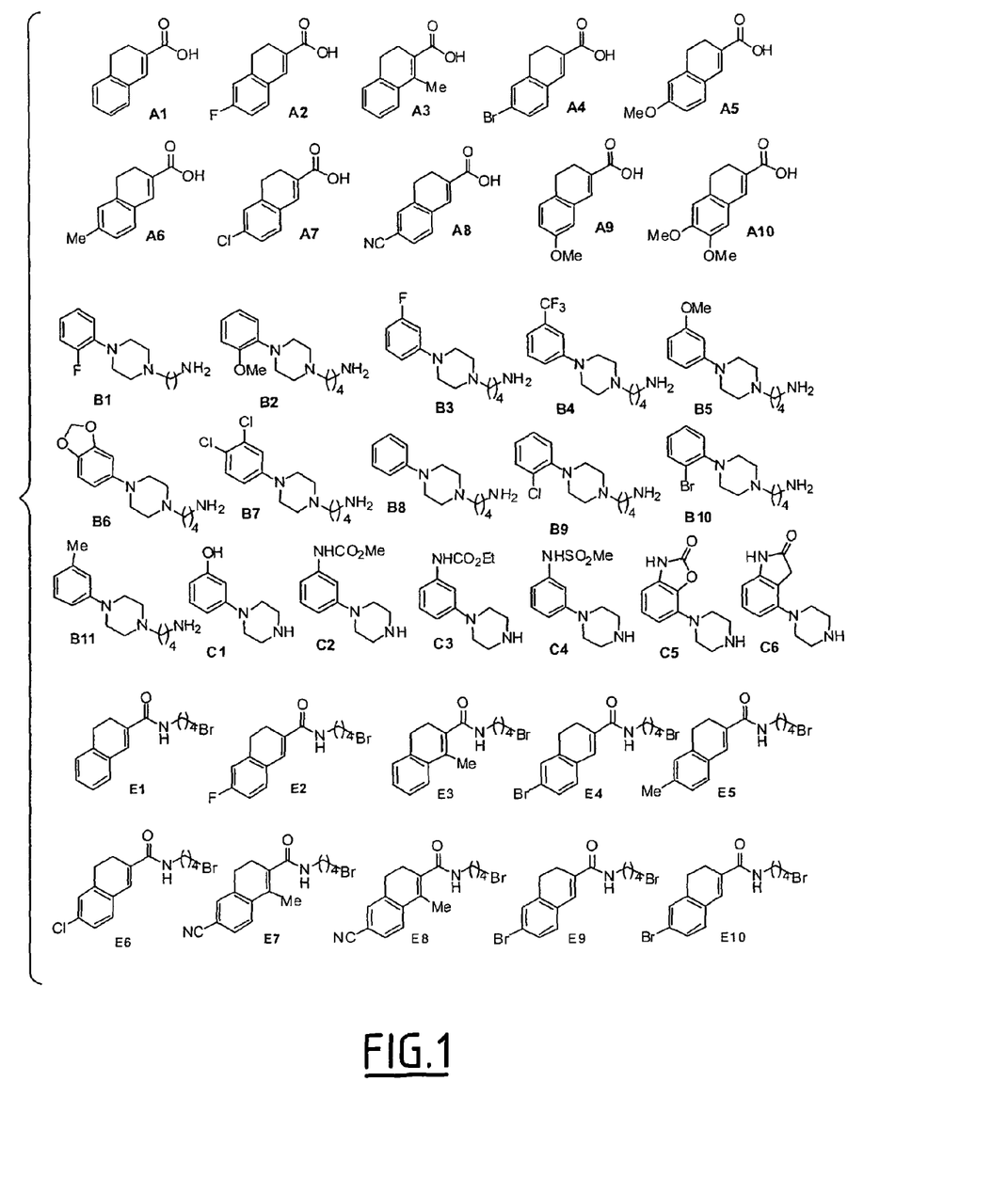
FIG. 1 displays the structure of the 3,4-dihydro-2-naphtoic acids (A1-A10), of the amine (B1-B11), of the piperazines (C1-C6), and bromo-derivatives (E1-E10) used for the synthesis of the compounds I-1 to I-28 exemplified in the instant application.
Figure 2:
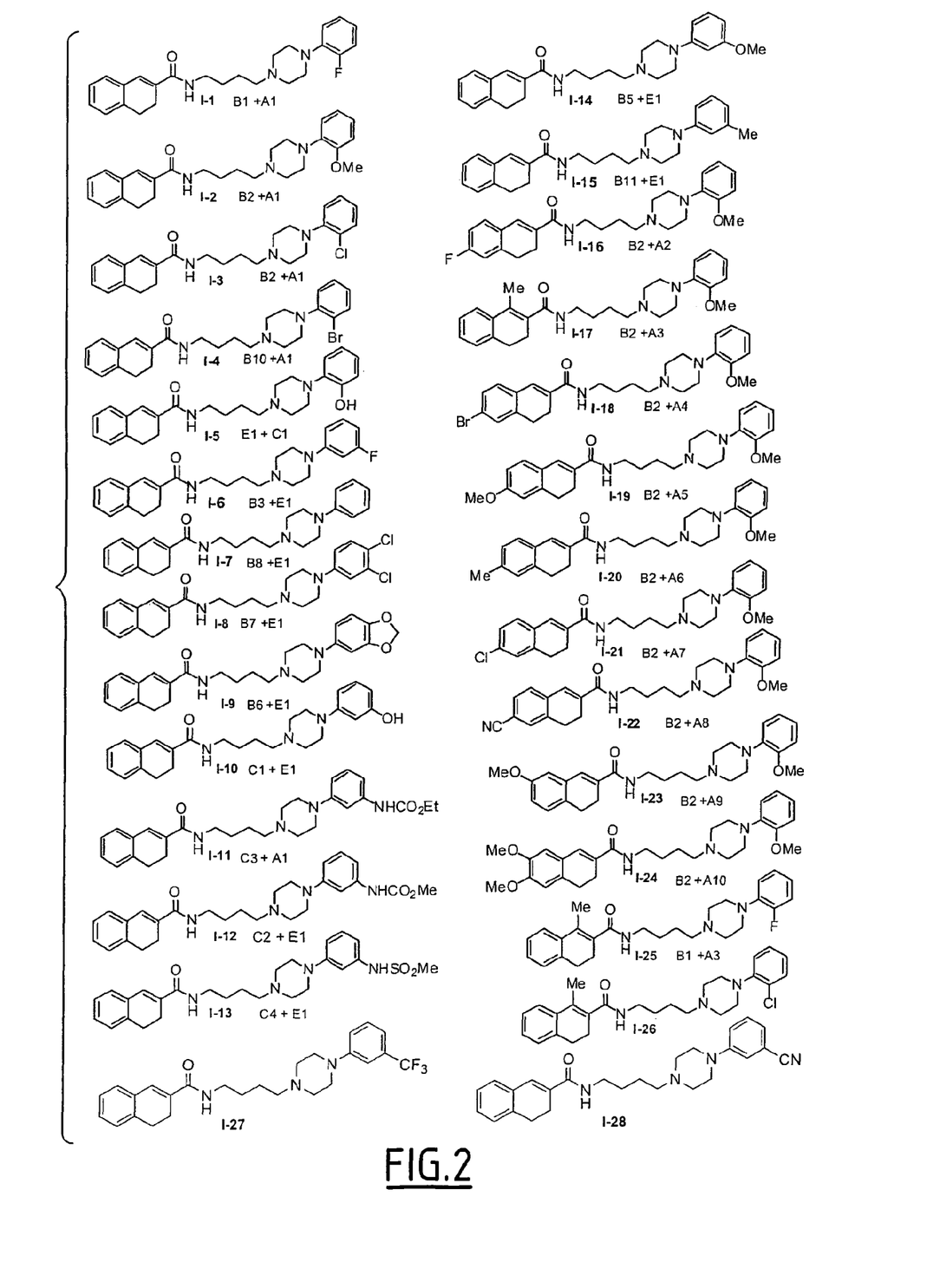
FIG. 2 shows the structure of the compounds I-1 to I-28 exemplified in the instant application.
Figure 3:
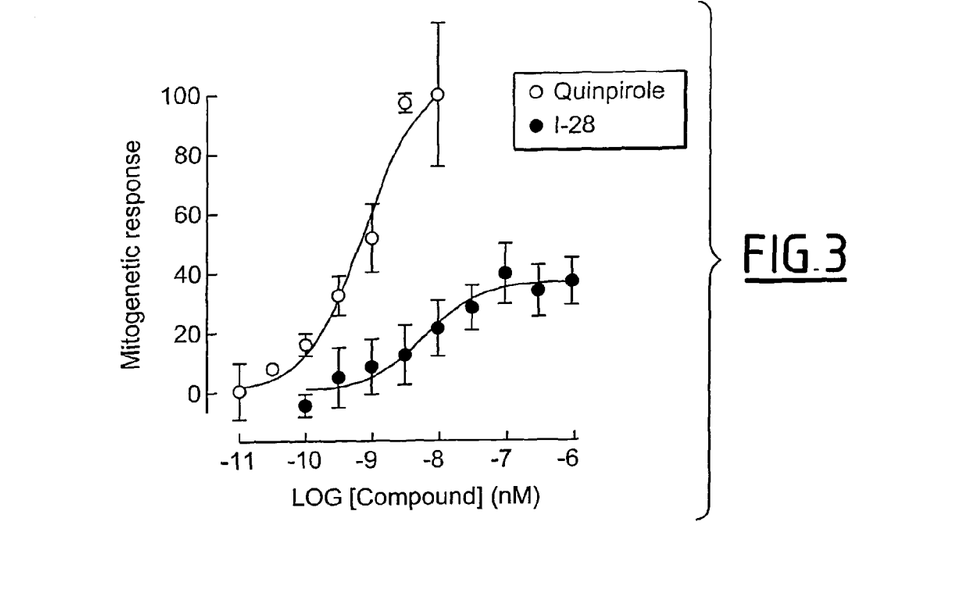
FIG. 3 displays the in vitro effect of I-28 and quinpirole (a full D3 receptor agonist) on mitogenesis in cells transfected with the human D3 receptor. Values are means (±SEM) of 10-12 determinations obtained in 4 independent experiments.

I-28 was found to induce mitogenesis in NG 108-15 cells transfected with the human D3 receptor. The maximal response was 37±2% of that produced by the full agonist quinpirole, with an EC50 value of 6.3 nM (FIG. 3).

Example 8

In vivo Activity of I-28 on Spontaneous Locomotor Activity of MK-801-induced Hyperactivity in Mice Activity of I-28 in vivo was assessed by using a simple test recently developed (Leriche et al. 2003 and international PCT application WO 2004/084952).

Animals.

Male Swiss mice (Charles River, France), weighing 26-28 g, were housed six per cage (25×15×13 cm), on a 12 h/12 h light/dark cycle (lights on at 07:00 a.m.), with food and water freely available. Room temperature ranged from 20° C. to 22° C. and humidity varied between 55% and 65%.

Drugs and Drug Administration.

Dizocilpine (MK-801) [(+)-5-methyl-10,11-dihydro-5H-dibenzo[a,d]cyclohepten-5,10-imine maleate] (Sigma) was dissolved in saline (0.9% NaCl). I-28 was dissolved in a few drops of HCl and distilled water, and the pH of the solution was adjusted to pH 5 using NaOH. The doses of I-28 are expressed as the weight of the base. The compounds were injected i.p. in a volume of 5 ml·kg$^{-1}$.

Locomotor Activity.

All experiments were conducted between 2.00 p.m. and 6.00 p.m., and the animals were kept in the test room at least 1 hour before recording their activity. The locomotor activity was measured in an actimeter that was composed of eight individual activity cages (30×15×18 cm, with sawdust on the floor) transected by infrared beams (Imetronic, Pessac, France). Counts for forward horizontal activity were incremented each time the animal moved from one-half part of the cage to the other, corresponding to disruption of two crossed parallel beams distant of 14 cm. In time-course studies, counts were summed every 5 minute.

Mice were injected with either Vehicle (distilled water pH 5) or I-28 (0.1, 0.3, 1 or 3 mg·kg$^{-1}$), and their horizontal locomotor activity was measured for 30 minutes (spontaneous locomotor activity). They were subsequently treated with saline or MK-801 (0.12 mg·kg$^{-1}$) and the activity was measured for 1 hour (MK-801-induced locomotor activity).

I-28 had no effect on spontaneous locomotor activity during habituation up to the dose of 3.0 mg·kg$^{-1}$. At this dose, it weakly inhibited the spontaneous activity (−25%, P=0.042, by LSD post-hoc test).

Figure 4:
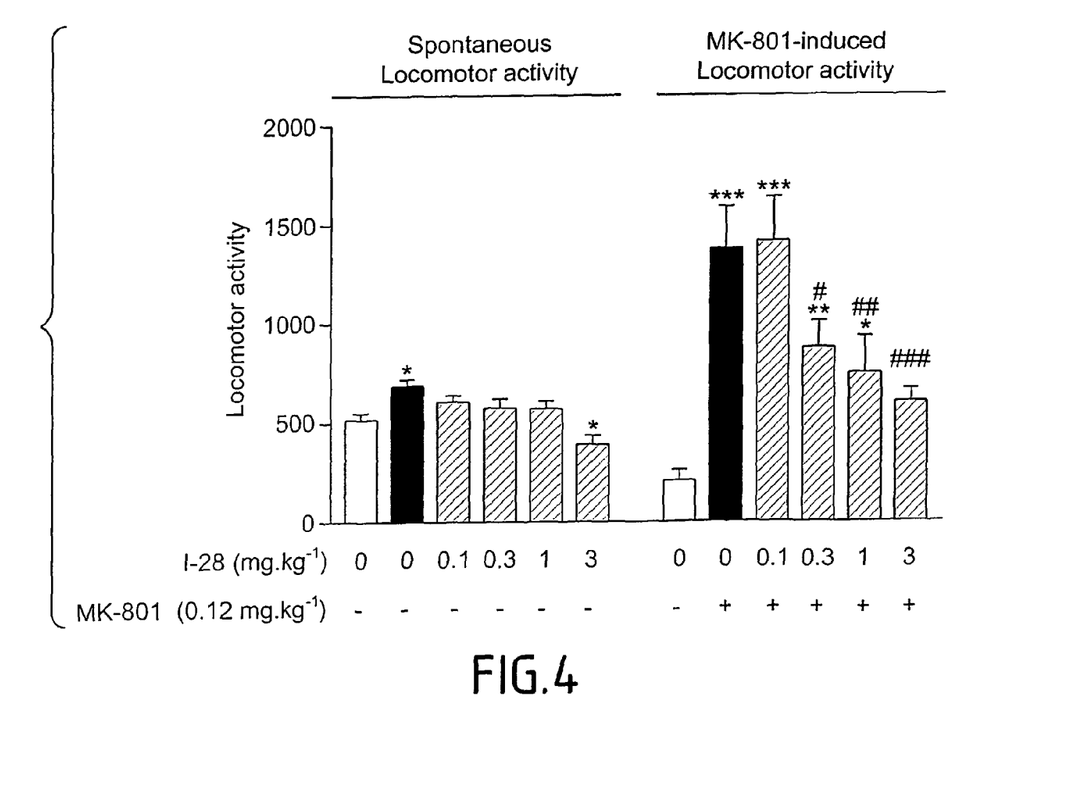
FIG. 4 shows the in vivo effect of I-28 on spontaneous activity during the habituation phase (left part of the panels) and on MK-801-induced horizontal locomotor activity (right part of the panels). *$P<0.05$; $P<0.01$; *$P<0.005$ vs. Saline-pretreated, vehicle-treated animals. #$P<0.05$; ##$P<0.01$: ###$P<0.005$ vs. Saline-pretreated, MK-801-treated animals by ANOVA following LSD post-hoc test.

MK-801 clearly inducted hyperactivity (P<0.000005 vs. saline+vehicle, by LSD post-hoc test). I-28 inhibited MK-801-induced hyperactivity dose-dependently and almost completely, with an ED$_{50}$ of about 0.3 mg·kg$^{-1}$. There was a significant effect of dose ($F_{5,54}$=8.23, P=0.000008, by ANOVA). Moreover, at the doses of 0.3, 1.0 and 3.0 mg·kg$^{-1}$, there was significant inhibition of MK-801-induced hyperactivity (36.7%, P=0.031; 46.6%, P=0.0073 and 57.3%, P=0.0012 respectively, by LSD post-hoc test). Furthermore, at the 3.0 mg·kg$^{-1}$ dose the locomotor activity was not statistically different from this of the saline-pretreated, vehicle-treated group (P=0.10 by LSD post-hoc test). The results are summarized in FIG. 4.

Therefore, I-28 was found to be a potent partial agonist of recombinant human D3 receptor in vitro, with an intrinsic activity of 0.37. It had thus a lower intrinsic activity than that of BP 897 (intrinsic activity of 0.55).

Furthermore, I-28 was found to be a potent D3 receptor blocker in vivo. I-28 dose-dependently and largely inhibited MK-801-induced hyperactivity, with an ED$_{50}$ value of about 0.3 mg·kg$^{-1}$ i.p. The results demonstrate that I-28 is active after systemic administration and crosses the blood-brain barrier.

Thus, I-28 and the other compounds according to the invention may provide medication for the treatment of schizophrenia and other D3 receptor-related disorders.

REFERENCES

Arroyo M, Markou A, Robbins T W, Everitt B J (1999) Acquisition, maintenance and reinstatement of intravenous cocaine self-administration under a second-order schedule of reinforcement in rats: effects of conditioned cues and continuous access to cocaine. Psychopharmacology 140:331-344.

Association AP (2000) Diagnostic and Statistical Manual of Mental Disorders. In: (Association. AP, ed). Washington D.C.

Bezard E, Ferry S, Mach U, Leriche L, Boraud T, Stark H, Gross C, Sokoloff P (2003) Attenuation of levodopa-induced dyskinesia by normalizing dopamine D3 receptor function. Nat Med 6:762-767.

Childress A R, Mozley P D, McElgin W, J. F, Reivich M, O'Brien C P (1999) Limbic activation during cue-induced cocaine craving. Am J Psychiatry 156:11-18.

Deroche-Gamonet V, Belin D, Piazza P V (2004) Evidence for addiction-like behavior in the rat. Science 305:1014-1017.

Frances H, Foll B L, Diaz J, Smirnova M, Sokoloff P (2004) Role of DRD3 in morphine-induced conditioned place preference using drd3-knockout mice. Neuroreport 15:2245-2249.

Goldberg S R, Gardner M L (1981) Second-order schedules: extended sequences of behavior controlled by brief environmental stimuli associated with drug self-administration. NIDA Res Monogr 37:241-270.

Hackling A, Ghosh R, Perachon S, Mann A, Holtje H D, Wermuth C G, Schwartz J C, Sippl W, Sokoloff P, Stark H (2003) N-(omega-(4-(2-methoxyphenyl)piperazin-1-yl) alkyl)carboxamides as dopamine D2 and D3 receptor ligands. J Med Chem 46:3883-3899.

Hamprecht B, Glaser T, Reiser G, Bayer E, Propst F. Culture and characteristics of hormone-responsive neuroblastoma X glioma hybrid cells. Methods Enzymol. 109: 316-341, 1985.

Kapur S, Mann J (1992) Role of the dopaminergic system in depression. Biol Psychiatry 32:1-17.

Koob G F (1992) Dopamine, addiction and reward. Sem Neurosci 4:139-148.

Lacroix L P, Hows M E, Shah A J, Hagan J J, Heidbreder C A (2003) Selective antagonism at dopamine D3 receptors enhances monoaminergic and cholinergic neurotransmission in the rat anterior cingulate cortex. Neuropsychopharmacology 28:839-849.

Lammers C H, Diaz J, Schwartz J-C, Sokoloff P (2000) Selective increase of dopamine D3 receptor gene expression as a common effect of chronic antidepressant treatments. Mol Psychiatry 5:378-388.

Le Foll B, Schwartz J-C, Sokoloff P (2003) Disruption of nicotine conditioning by dopamine D3 receptor ligands. Mol Psychiatry 8:225-230.

Le Foll B, Francés H, Diaz J, Schwartz J-C, Sokoloff P (2002) Role of the dopamine D3 receptor in reactivity to cocaine-associated cues in mice. Eur J Neurosci 15:2016-2026.

Leopoldo M, Berardi F, Colabufo N A, De Giorgio P, Lacivita E, Perrone R, Tortorella V (2002) Structure-affinity relationship study on N-[4-(4-arylpiperazin-1-yl)butyl]arylcarboxamides as potent and selective dopamine D(3) receptor ligands. J Med Chem 45:5727-5735.

Leriche L, Schwartz J C, Sokoloff P (2003) The dopamine D3 receptor mediates locomotor hyperactivity induced by NMDA receptor blockade. Neuropharmacology 45:174-181.

Lucotte G, Funalot B, Sokoloff P (2004) Allele-2 of the Ser-9-Gly polymorphism in the dopamine D3 receptor gene is responsible for the most common form of familial essential tremor. 8th International Congress of Parkinson's disease and movement disorders, Rome, June 2004. Abstract N° 1020.

Pilla M, Perachon S, Sautel F, Gamido F, Mann A, Wermuth C G, Schwartz J-C, Everitt B J, Sokoloff P (1999) Selective inhibition of cocaine-seeking behaviour by a partial dopamine D3 receptor agonist. Nature 400:371-375.

Pilon C, Lévesque D, Dimitriadou V, Griffon N, Martres M P, Schwartz J-C, Sokoloff P (1994) Functional coupling of the human dopamine D3 receptor in a transfected NG 108-15 neuroblastoma-glioma hybrid cell line. Eur J Pharmacol [Mol Pharmacol Sect] 268:129-139.

Robinson T E, Berridge K C (1993) The neural basis of drug craving: an incentive-sensitization theory of addiction. Brain Research Reviews 18:247-291.

Salamone J D (1994) The involvement of nucleus accumbens dopamine in appetitive and aversive motivation. Behav Brain Res 61:117-133.

Sautel F, Griffon N, Lévesque D, Pilon C, Schwartz J-C, Sokoloff P (1995) A functional test identifies dopamine agonists selective for D3 versus D2 receptors. Neuroreport 6:329-332.

Schoenberg A, Heck R F (1974) Palladium-catalyzed amidation of aryl, heterocyclic, and vinylic halides. J Org Chem 39:3327-3331.

Schwartz J C (2003) The dopamine D3 receptor as a therapeutic target. Eur Neuropsychopharmacol 13 (Suppl. 4):S166.

Sokoloff P, Andrieux M, Besançon R, Pilon C, Martres M-P, Giros B, Schwartz J-C (1992) Pharmacology of human D3 dopamine receptor expressed in a mammalian cell line: comparison with D2 receptor. Eur J Pharmacol Mol Pharmacol Sect 225:331-337.

Sokoloff P, Diaz J, Levesque D, Pilon C, Dimitriadou V, Griffon N, Lammers C H, Martres M P, Schwartz J C (1995) Novel dopamine receptor subtypes as targets for antipsychotic drugs. Annals New York Academy of Sciences 757:278-292.

Staley J K, Mash D C (1996) Adaptive increase in D3 dopamine receptors in the brain reward circuits of human cocaine fatalities. J Neurosci 16:6100-6106.

Vanderschuren L J, Everitt B J (2004) Drug seeking becomes compulsive after prolonged cocaine self-administration. Science 305:1017-1019.

Vebrel J, Carrie R (1982) Synthesis of methoxycarbonylated indenes, 1,2-dihydronaphthalenes, and benzocycloheptene. Preparation of the starting 1-indanones, 1-tetralones, and benzosuberone. Bull. Soc. Chim. Fr., 3-4: 116.

Vorel S R, Ashby C R J, Paul M, Liu X, Hayes R, Hagan J J, Middlemiss D N, Stemp G, Gardner E L (2002) Dopamine D3 receptor antagonism inhibits cocaine-seeking and cocaine-enhanced brain reward in rats. J Neurosci 22:9595-9603.

Wenkert E, Greenfield S A, (1967) 1-Methyl-2-tetralone. Chemistry & Industry (London, U. K.) 29:1252

Willner P (1997) The mesolimbic dopamine system as a target for rapid antidepressant action. Int Clin Psychopharmacology 12:S7-S14.

Wolfe J P, Timori H, Sadighi J P, Yin J, Buchwald S L (2000), Simple, efficient catalyst system for the palladium-catalyzed amination of aryl chlorides, bromides, and triflates. J Org Chem 5:1158-1174

The invention claimed is:

1. Compound of formula (I)

in which $R^1$ and $R^2$ can be identical or different and each independently represent a hydrogen, a halogen atom, or a hydroxyl, alkoxy, nitrile, nitro or perfluoroalkyl group, or an alkyl group, eventually substituted, $R^1$ and $R^2$ substituents both being attached to the same ring of the aromatic ring of the dihydronaphthyl moiety, $R^3$ represents a hydrogen or an alkyl group in the C-1, C-3 or C-4 position of the non-aromatic ring of the dihydronaphthyl moiety in formula (I), $R^4$ and $R^5$ can be identical or different and each independently represent a hydrogen, a halogen atom, or a hydroxyl, alkoxy, nitrile, nitro, alkylthio, alkylsulfonyl, sulfoamido, carboxyamido, acetyl, hydroxyalkyl, or perfluoroalkyl group in formula (I), $R^4$ and $R^5$ also may form together a ring fused with the phenyl ring forming heterocyclic compounds in formula (I), and salts thereof.

2. A compound according to claim 1, in which:

$R^1$ and $R^2$ can be identical or different and each independently represent a hydrogen, bromine, chlorine or fluorine atom, or a hydroxyl, methoxy, nitrile, nitro or trifluoromethyl group, or an alkyl group, eventually substituted, $R^1$ and $R^2$ substituents both being attached to the same ring of the aromatic ring of the dihydronaphthyl moiety, $R^3$ represents a hydrogen or an alkyl group in the C-1, C-3 or C-4 position of the non-aromatic ring of the dihydronaphthyl moiety in formula (I), $R^4$ and $R^5$ can be identical or different and each independently represent a hydrogen, bromine, chlorine or fluorine atom, or a hydroxyl, methoxy, nitrile, nitro, methylthio, methylsulfonyl sulfoamido, carboxyamido, acetyl, hydroxymethyl, or trifluoromethyl group in formula (I), $R^4$ and $R^5$ also may form together a ring fused with the phenyl ring forming heterocyclic moieties in formula (I).

3. A compound according to claim 1, wherein $R^1$ represents a hydrogen atom, bromine, chlorine or fluorine atom, or a methoxy, or cyano group, or a methyl residue.

4. A compound according to claim 1, wherein $R^2$ represents a hydrogen atom or a methoxy group.

5. A compound according to claim 1, wherein $R^3$ represents a hydrogen atom or a methyl residue in the C-1, C-3 or C-4 position on the dihydronaphthyl moiety in formula (I).

6. A compound according to claim 1, wherein $R^4$ represents a hydrogen, or chlorine atom, or forms together with $R^5$ a ring fused with the phenyl ring forming heterocyclic moieties in formula (I).

7. A compound according to claim 1, wherein $R^5$ represents a hydrogen, bromine, chlorine or fluorine atom, or a hydroxyl, methoxy, nitrile, trifluoromethyl, ethoxycarbamoyl, methoxycarbamoyl or methylsulfamido group, or a methyl residue, or forms together with $R^4$ part of a ring fused with the phenyl ring forming heterocyclic moieties in formula (I).

8. A compound according to claim 1, wherein $R^4$ is a hydrogen atom, and $R^5$ is in C-3 or C-5 position of the phenyl ring.

9. A compound according to claim 1, which is selected from the group consisting of:

N-[4-(2-fluorophenyl)piperazin-1-yl)butyl]-3,4-dihydro-2-naphthamide,

N-[4-(2-methoxyphenyl)piperazin-1-yl)butyl]-3,4-dihydro-2-naphthamide

N-[4-(2-chlorophenyl)piperazin-1-yl)butyl]-3,4-dihydro-2-naphthamide,

N-[4-(2-bromophenyl)piperazin-1-yl)butyl]-3,4-dihydro-2-naphthamide,

N-[4-(2-hydroxyphenyl)piperazin-1-yl)butyl]-3,4-dihydro-2-naphthamide,

N-[4-(3-fluorophenyl)piperazin-1-yl)butyl]-3,4-dihydro-2-naphthamide,

N-[4-phenyl)piperazin-1-yl)butyl]-3,4-dihydro-2-naphthamide,

N-[4-(3,4-dichlorophenyl)piperazin-1-yl)butyl]-3,4-dihydro-2-naphthamide,

N-[4-(2,3-methylenedioxyxyphenyl)piperazin-1-yl)butyl]-3,4-dihydro-2-naphthamide, N-[4-(3-hydroxyphenyl)piperazin-1-yl)butyl]-3,4-dihydro-2-naphthamide N-[4-(N-3-ethoxycarbamoylphenyl)piperazin-1-yl)butyl]-3,4-dihydro-2-naphthamide, N-[4-(N-3-methoxycarbamoylphenyl)piperazin-1-yl)butyl]-3,4-dihydro-2-naphthamide, N-[4-(N-3-methylsulfamidophenyl)piperazin-1-yl)butyl]-3,4-dihydro-2-naphthamide, N-[4-(3-methoxyphenyl)piperazin-1-yl)butyl]-3,4-dihydro-2-naphthamide N-[4-(3-methylphenyl)piperazin-1-yl)butyl]-3,4-dihydro-2-naphthamide N-[4-(2-methoxyphenyl)piperazin-1-yl)butyl]-3,4-dihydro-6-fluoro-2-naphthamide N-[4-(2-methoxyphenyl)piperazin-1-yl)butyl]-1-methyl-3,4-dihydro-2-naphthamide, N-[4-(2-methoxyphenyl)piperazin-1-yl)butyl]-3,4-dihydro-6-bromo-2-naphthamide, N-[4-(2-methoxyphenyl)piperazin-1-yl)butyl]-3,4-dihydro-6-methoxy-2-naphthamide, N-[4-(2-methoxyphenyl)piperazin-1-yl)butyl]-3,4-dihydro-6-methyl-2-naphthamide, N-[4-(2-methoxyphenyl)piperazin-1-yl)butyl]-3,4-dihydro-6-chloro-2-naphthamide, N-[4-(2-methoxyphenyl)piperazin-1-yl)butyl]-3,4-dihydro-6-cyano-2-naphthamide, N-[4-(2-methoxyphenyl)piperazin-1-yl)butyl]-3,4-dihydro-7-methoxy-2-naphthamide, N-[4-(2-methoxyphenyl)piperazin-1-yl)butyl]-3,4-dihydro-6,7-dimethoxy-2-naphthamide, N-[4-(2-fluorophenyl)piperazin-1-yl)butyl]-1-methyl-3,4-dihydro-2-naphthamide, N-[4-(2-chlorophenyl)piperazin-1-yl)butyl]-1-methyl-3,4-dihydro-2-naphthamide, N-[4-(3-trifluormethylphenyl)piperazin-1-yl)butyl]-3,4-dihydro-2-Naphthamide, and N-[4-(3-cyanophenyl)piperazin-1-yl)butyl]-3,4-dihydro-2-naphthamide.

10. A pharmaceutical composition comprising at least one compound according to claim 9, in combination with a pharmaceutically acceptable carrier.

11. A method of treatment of a neuropsychological disorder which comprises administering a compound according to claim 1 to a patient in need thereof, wherein the neuropsychological disorder is selected from the group consisting of Parkinson's disease, schizophrenia, and depression.

\* \* \* \* \*